United States Patent
Bell

(10) Patent No.: US 9,993,027 B1
(45) Date of Patent: Jun. 12, 2018

(54) HEATER ELEMENT FOR A VAPORIZATION DEVICE

(71) Applicant: Funai Electric Co., Ltd., Osaka (JP)

(72) Inventor: Byron V. Bell, Lexington, KY (US)

(73) Assignee: Funai Electric Co., Ltd. (JP)

( * ) Notice: Subject to any disclaimer, the term of this patent is extended or adjusted under 35 U.S.C. 154(b) by 0 days. days.

(21) Appl. No.: 15/369,961

(22) Filed: Dec. 6, 2016

(51) Int. Cl.
| | |
|---|---|
| *A24F 17/00* | (2006.01) |
| *A24F 47/00* | (2006.01) |
| *H05B 3/44* | (2006.01) |
| *A61M 11/04* | (2006.01) |
| *A61M 15/00* | (2006.01) |

(52) U.S. Cl.
CPC ......... *A24F 47/008* (2013.01); *A61M 11/042* (2014.02); *A61M 15/0021* (2014.02); *H05B 3/44* (2013.01)

(58) Field of Classification Search
CPC ............... A24F 47/008; A61M 11/042; A61M 15/0021; H05B 3/44
USPC ........................................................ 131/329
See application file for complete search history.

(56) References Cited

U.S. PATENT DOCUMENTS

| | | | |
|---|---|---|---|
| 9,872,520 B1 * | 1/2018 | Elson | .................... A24F 47/008 |
| 2003/0007035 A1 | 1/2003 | Pan | |
| 2009/0032034 A1 | 2/2009 | Steinberg | |
| 2011/0226236 A1 | 9/2011 | Buchberger | |
| 2013/0220314 A1 | 8/2013 | Bottom | |
| 2015/0114409 A1 | 4/2015 | Brammer et al. | |
| 2015/0208728 A1 | 7/2015 | Lord | |
| 2016/0309785 A1 | 10/2016 | Holtz | |
| 2017/0347714 A1 | 12/2017 | Metz et al. | |

FOREIGN PATENT DOCUMENTS

EP      0845220 A1    6/1998

OTHER PUBLICATIONS

Brooks, D.; Selvy, A, "A high dielectric constant lets these heating modules be compact and heat up quickly," Basics of Ceramic Heaters, Aug. 28, 2013, pp. 1-3.
Wojcik, T.M., "Heat Transfer Crises on Sintered Porous Surfaces-Experimental Investigations," EPJ Web Conferences 25, 02031, 2012, pp. 1-7.
"Alumina Metallic Ceramic Heating Element (HTCC)," Industrial Ceramics Web pages, Aug. 12, 2016, pp. 1-6.
"Laser Services and Inspection for Thin-Film Ceramic Substrates," CoorsTek, Inc., Web Pages, Aug. 28, 2013, pp. 1-11.
"Technical Data Sheet HTC-300 High Temperaure Carbon Black," Conductive Compounds Web page, Feb. 3, 2016, pp. 1-2.
"Thin Film Heaters," Thermo-Stone, web page 2008-2012, pp. 1-4.
"Thick-Film Material and Ceramic Tapes From ESL Electroscience," ESL ElectroScience, web pages Aug. 12, 2016, pp. 1-2.

* cited by examiner

*Primary Examiner* — Khiem Nguyen
(74) *Attorney, Agent, or Firm* — Luedeka Neely Group, PC

(57) ABSTRACT

A heating element for a vaporizing device, a vaporizing device containing the heating element, and a method for vaporizing fluid ejected by an ejection head. The heating element includes a conductive material deposited onto an insulative substrate, a protective layer deposited onto the conductive layer, and a porous layer having a porosity of at least about 50% deposited onto the protective layer. The heating element has an effective surface area (ESA) for fluid vaporization that is greater than a planar surface area defined by dimensions of the heating element so that a fluid contact surface of the heating element is greater than the planar surface area of the heating element.

20 Claims, 4 Drawing Sheets

HEATER ELEMENT FOR A VAPORIZATION DEVICE

TECHNICAL FIELD

One of the applications of a fluidic ejection device is to jet a solution onto to another device where a secondary function may be performed. A common secondary function is to vaporize a solution using a heater such that the contents of the solution can be vaporized so as to deliver the solution as a gaseous substance. Applications of such technology include, but are not limited to, metering and vaporizing device for electronic cigarettes, vapor therapy, gaseous pharmaceutical delivery, vapor phase reactions for microlabs, and the like. A problem associated with such devices is efficient vaporization of the fluid. This document discloses improved heating elements and methods for improving the vaporization efficiency of heating elements for vaporization devices.

BACKGROUND AND SUMMARY

When jetting a fluid onto a heated surface it is highly desirable for 100% of the fluid to vaporize so that liquid is not discharged from the vaporizing device. The problem lies in that the vaporizing heater must be small enough to heat up extremely quickly, but yet has enough surface area to catch all fluid and fluid droplets that are being ejected onto the heating element. A typical metal foil heating element has a smooth surface with minimal liquid/heater interface which is due to a low surface roughness of the heating element surface. Accordingly, some of the fluid droplets impinging on the surface of the heating element will be scattered or fluid droplets will be ejected from the heating element if a significant layer of fluid already exists on the surface of the heating element when new droplets arrive. Thus, instead of only vapor being discharged from the vaporization device, liquid droplets may be entrained in the vapor and discharged from the vaporization device. In some applications, the discharge of liquid is not only undesirable, but may be detrimental to the user. Also, unvaporized fluid may build up inside the vaporization device and thus degrade the operation of the device.

In order to avoid the discharge of liquid droplets from a vaporization device, the stream of fluid ejected onto the surface of the heating element must be efficiently captured by the heating element, spread out over the surface of the heating element, and completely vaporized at approximately the same rate as the fluid arrives on the surface of the heating element in order to avoid liquid accumulation on the surface of the heating element.

In view of the foregoing, embodiments of the disclosure provide a heating element for a vaporizing device, a vaporizing device containing the heating element, and a method for vaporizing fluid ejected by an ejection head. The heating element includes a conductive material deposited onto an insulative substrate, a protective layer deposited onto the conductive layer, and a porous layer having a porosity of at least about 50% deposited onto the protective layer. The heating element has an effective surface area (ESA) for fluid vaporization that is greater than a planar surface area defined by dimensions of the heating element so that a fluid contact surface of the heating element is greater than the planar surface area of the heating element.

In one embodiment, the heating element has a rectangular shape. Accordingly, the effective surface area (ESA) of the heating element is defined by the equation $ESA > L \times W$, wherein L is a length of the heating element and W is a width of the heating element that is exposed to a vaporizing fluid.

In another embodiment, the heating element has a circular shape. Accordingly, the effective surface area (ESA) of the heating element is defined by the equation $ESA > \Pi \times R^2$ wherein R is a radius of the heating element that is exposed to a vaporizing fluid.

Another embodiment of the disclosure provides a vaporizing device that includes a housing body, a mouthpiece attached to the housing body, and a heating element disposed adjacent to the mouthpiece for vaporizing fluid ejected from an ejection head. The heating element has a conductive material deposited onto an insulative substrate, a protective layer deposited onto the conductive layer, and a porous layer having a porosity of at least about 50% deposited onto the protective layer.

A further embodiment of the disclosure provides a method for vaporizing a fluid ejected by an ejection head so that substantially all of the fluid ejected by the ejection head is vaporized. The method includes providing a vaporization device having an ejection head and a vaporizing heater element adjacent to the ejection head; ejecting fluid onto the heater element; activating the heating element during fluid ejection; and vaporizing substantially all of the fluid using the heating element. The heating element has a conductive material deposited on an insulative substrate, a protective layer deposited on the conductive layer, and a porous layer having a porosity of at least about 50% deposited onto the protective layer.

In some embodiments, the porous layer has a grit blasted surface texture that provides the effective surface area (ESA) thereof. In other embodiments, the porous layer is a grit blasted ceramic material.

In another embodiment, the porous layer is a laser etched ceramic layer.

In yet another embodiment, the porous layer is deposited as a coarse glass frit that is sintered onto a surface of the heating element.

In some embodiments, the porous layer has a thickness ranging from about 0.5 millimeters (mm) to about 3 mm. In other embodiments the porous layer has a thickness ranging from about 1 mm to about 2 mm.

In some embodiments, the insulative substrate, conductive layer and protective layer have a combined thickness ranging from about 4 millimeters (mm) to about 1 centimeter (cm)

In some embodiments, the porous layer has a porosity ranging from about 50% to about 95%.

In some embodiments, the conductive layer is a screen printed conductive layer deposited onto a ceramic substrate.

BRIEF DESCRIPTION OF THE DRAWINGS

Other features and advantages of disclosed embodiments may be evident by reference to the following detailed description, drawings and claims wherein:

DETAILED DESCRIPTION OF EMBODIMENTS

Figure 1:
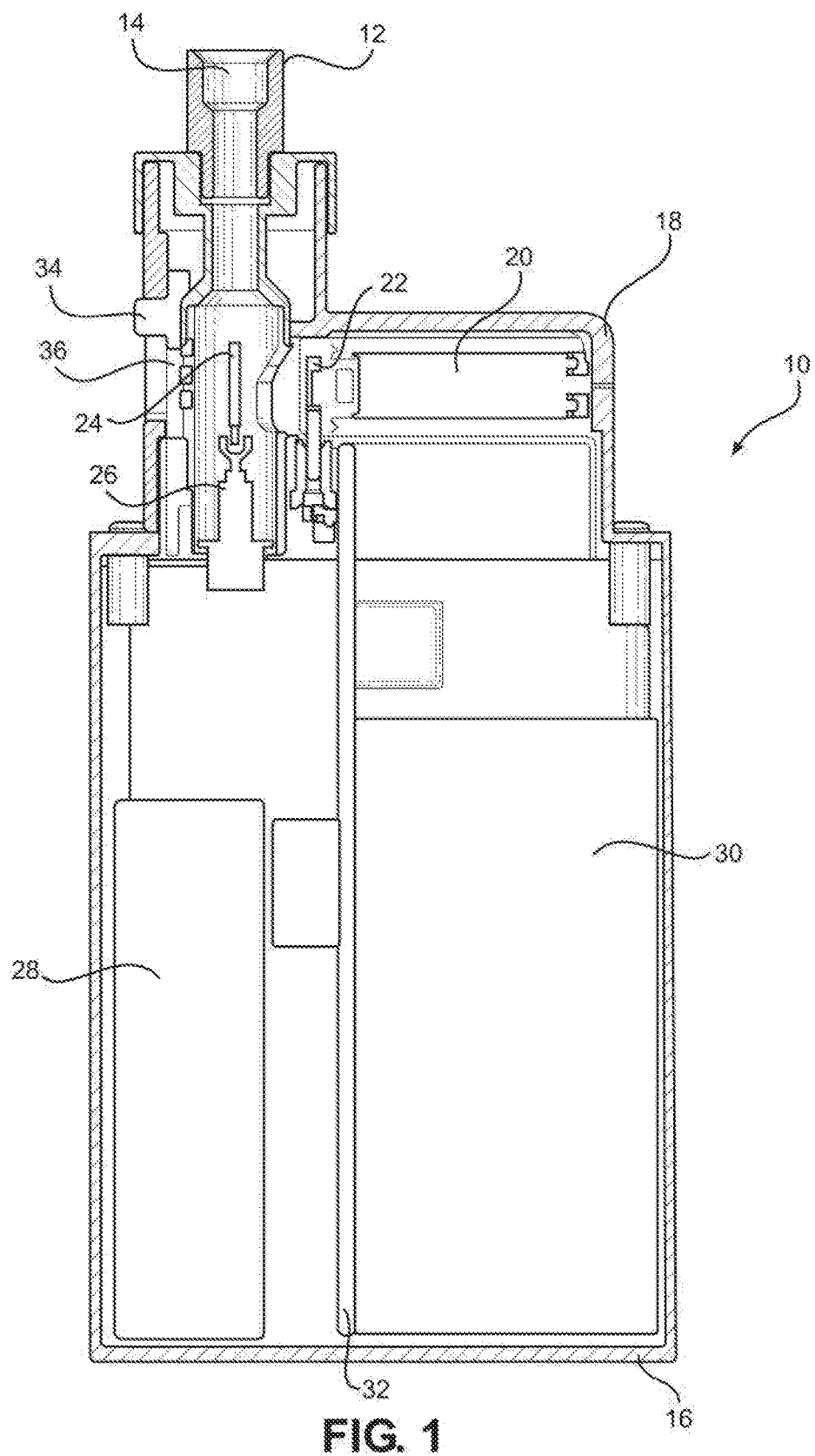
FIG. 1 is a cross-sectional view, not to scale, of a vaporization device according to an embodiment of the disclosure.
Figure 2:
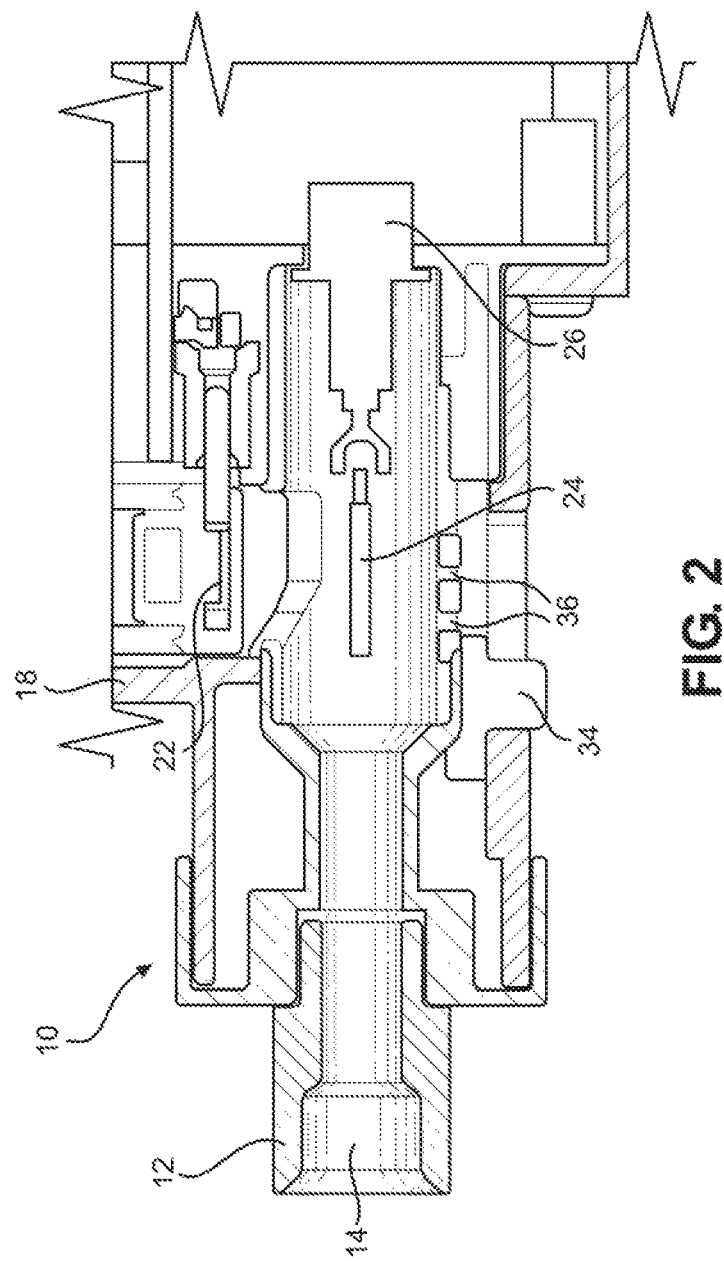
FIG. 2 is a close-up view, not to scale, of a portion of the vaporization device of FIG. 1.

The disclosure is directed to a vaporization device 10 as shown in FIGS. 1 and 2 and heating elements therefor as shown in FIGS. 3-8. Such devices 10 may be used for a wide variety of applications wherein a liquid is ejected onto a heating element to provide a vapor stream as described in more detail below. Such devices 10 are typically hand held devices such as electronic cigarettes that have a mouthpiece 12 for inhaling vapors generated by the device 10. The mouthpiece 12 includes a conduit 14 for flow of vapors out of the device 10. The main components of the device 10 include a housing body 16, a removable cartridge cover 18, a removable fluid supply cartridge 20, an ejection head 22 associated with the fluid supply cartridge 20, and a heating element 24 and holder therefor 26 for vaporizing fluid ejected from the ejection head 22. Other components associated with the vaporization device 10 include a rechargeable power supply 28, a main circuit board 30, and a vaporization driver card 32. An enlarged portion of the vaporization device is shown in FIG. 2.

The mouthpiece 12, as well as the body 16 of the vaporization device 10 may be made from a wide variety of materials including plastics, metals, glass, ceramic and the like provided the materials are compatible with the fluids to be ejected and vaporized by the device 10. A particularly suitable material may be selected from polyvinyl chloride, high density polyethylene, polycarbonate, stainless steel, surgical steel, nickel-plated steel, and the like. All parts, including the mouthpiece 12, and body 16 that come in contact with fluids and vapors may be made of plastic. The conduit 14 may be made of metal such as stainless steel or other material that is resistant to heat and vapors generated by the device.

As shown in FIG. 1, the housing body 16 may include the circuit board 30 and the driver card 32 for providing the logic circuitry for the heating element 24 (described in more detail below) and ejection head 22. The rechargeable battery 28 may also be housed in the housing body 16. In another embodiment, a removable, non-rechargeable battery may be housed in the housing body. Electrical contacts, such as a USB (not shown) may be used to recharge the battery 28 and to change program setting for the ejection head 22 and heating element 24. The microfluidic ejection head 22 is in fluid flow communication with the fluid supply cartridge 20 that provides fluid to be ejected by the ejection head 22.

An inlet air flow control device may be included to provide backpressure control on the ejection head 22. The inlet air flow control device may include a damper slide 34 and air inlet holes 36 that allow air to be drawn into the conduit 14 adjacent the heating element 24 and ejection head 22 so that excessive negative pressure on the ejection head 22 can be avoided.

Figure 3:
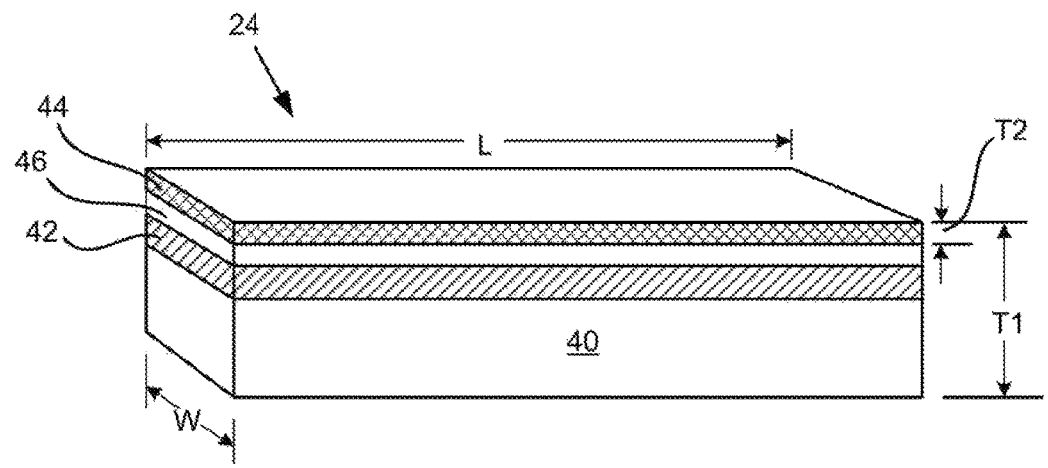
FIG. 3 is a cross-sectional view, not to scale, of a heating element according to an embodiment of the disclosure.

An important component of the vaporization device 10 is the heating element 24 as shown in FIG. 3. The heating element 24 is typically made of a high temperature solid ceramic base 40 having a resistive or conductive material 42 printed thereon, deposited thereon, or otherwise imbedded in the ceramic base 40. The resistive or conductive material may be selected from a wide variety of materials typically used for heating elements including, but not limited to, silver and/or carbon screen printed materials, as tungsten, molybdenum, molybdenum-manganese, and the like.

As set forth above, it is desirable to vaporize substantially all fluid ejected from the ejection head 22 so that only vapors are discharged through the conduit 14 of the mouthpiece 12. Accordingly, the heating element 24 desirably contains a fluid absorbing or capturing layer 44 that is formed on a protective layer 46. The protective layer 46 is positioned between the fluid absorbing or capturing layer 44 and the resistive or conductive metal material 42 and may be made of the same material as the ceramic base 40 or any other suitable, high temperature material that is substantially non-porous. Other suitable materials for the protective layer include, but are not limited to alumina, aluminum nitride, silica or silicon nitride.

The overall thickness T1 of the heating element may range from about four millimeters to about 1 centimeter. The thickness T2 of the fluid absorbing or capturing layer 44 may range from about 0.5 to about 3 millimeters in thickness, such as from about 1 to about 2 millimeters in thickness. The thicknesses of the resistive or conductive material 42 and protective layer 46 are not critical to the embodiments of the disclosure. In the case of an imbedded resistive or conductive material 42, a protective material layer 46 may not be necessary.

In one embodiment, as shown in FIG. 3, layer 44 is a porous layer having a porosity of at least about 50% that is deposited onto the protective layer 46. In another embodiment, the porosity of layer 44 may range from about 60% to about 85%. Having a porosity of at least about 50% means that the layer 44 is porous or has indentations or cavities that provide at least 50% void space volume relative to the entire volume of layer 44. The porosity range is based on engineering judgement as the practical limits for a porous layer. The mass of the layer 44 is as small as possible to optimize warm up speed and minimize power consumption for heating the layer 44. Low mass requires a high porosity with 95% chosen as a realistic upper limit. Above 95% porosity the structure would be too weak and difficult to fabricate. A 50% porosity is chosen as the minimum porosity for layer 44. Below 50% porosity wicking properties of layer 44 will suffer due to closed off/inaccessible pores in the structure.

For a rectangular heating element having a width W, a length L and a thickness T1 as described above, the heating element 24 is further defined as having an effective surface area (ESA) for fluid vaporization that is defined by the equation ESA>L×W. For a circular heating element, the effective surface area (ESA) of the heating element is defined by the equation ESA>Π×R$^2$ wherein R is a radius of the heating element that is exposed to a vaporizing fluid. The heating element is not limited to a rectangular or circular shape as any shape including triangular, complex shapes, and the like may be used. Accordingly, the ESA of the heating element is greater than the nominal dimensions of the protective layer 46.

Figure 4:
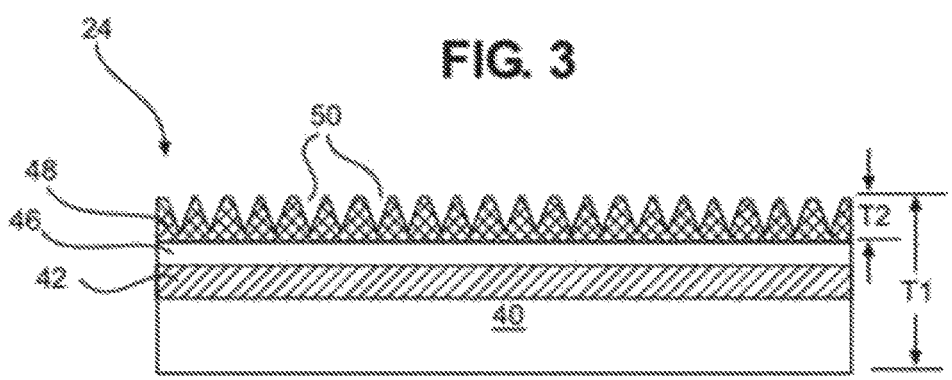
FIG. 4 is a cross-sectional view, not to scale, of a heating element according to another embodiment of the disclosure.

In another embodiment, as shown in FIG. 4, a grit blasted ceramic layer or a laser etched ceramic layer 48 may be used to capture the fluid ejected from the ejection head 22. Accordingly, a ceramic layer 48 may be applied to the protective layer 46 and then grit blasted or laser etched to form indentations 50 in the ceramic layer 48 that significantly increase the effective surface area of the heating element 24 as shown. In an alternative embodiment, the protective layer 46 itself may be grit blasted or laser etched as opposed to adding and blasting or etching layer 48. The grit blasted or laser etched surface of layer 48 or protective layer 46, like the porous layer 44, may be effective to prevent pooling of liquid on the surface thereof and may provide more rapid vaporization of fluid ejected onto the heating element 24.

Figure 5:
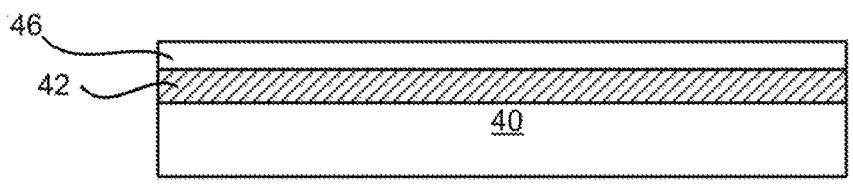
FIGS. 5-7 are schematic views, not to scale, of a process for making a heating element according to an embodiment of the disclosure.
Figure 6:
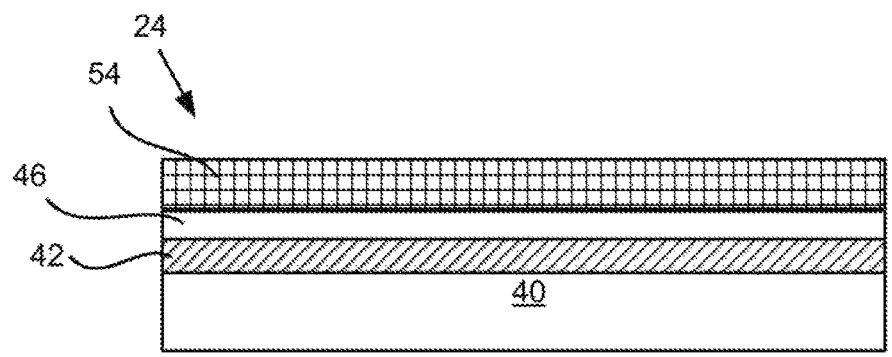
Figure 7:
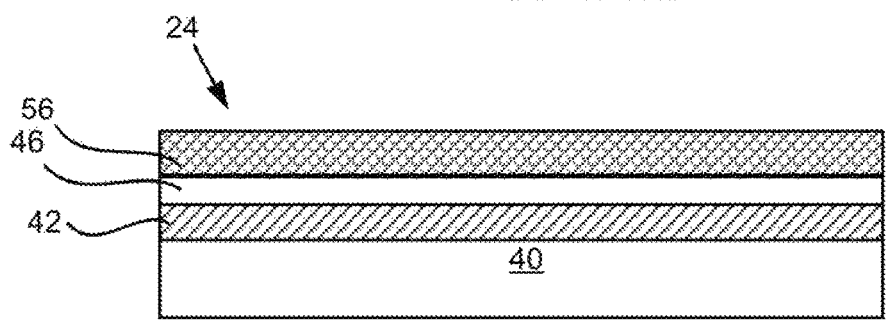

One method for making a heating element 24, according to an embodiment of the disclosure, is illustrated schematically in FIGS. 5-7. The heating element 24 includes a ceramic material 40 that contains a high melting point metal heating material such as tungsten, molybdenum, or molybdenum-manganese embedded in a 92 to 96% by weight alumina ceramic substrate 40 to from the conductive layer 42. For example, a metal heating resistance slurry of one or more of the foregoing metals may be printed onto a tape casting of a ceramic green body to form the conductive layer 42. Several layers of ceramic green body are then laminated together at a high temperature with the aid of 4 to 8% by weight of a sintering additive to form an alumina ceramic heating substrate 40. Materials for the ceramic substrate 40 include, but are not limited to aluminum nitride and cubic boron nitride.

In a next step of the process, as shown in FIG. 6, a layer of glass frit is applied to a the protective layer 46 that is applied to the conductive layer 46 to provide layer 54. The glass frit may be applied as a screen printed paste or slurry to the surface of the heating element 24.

Figure 8:
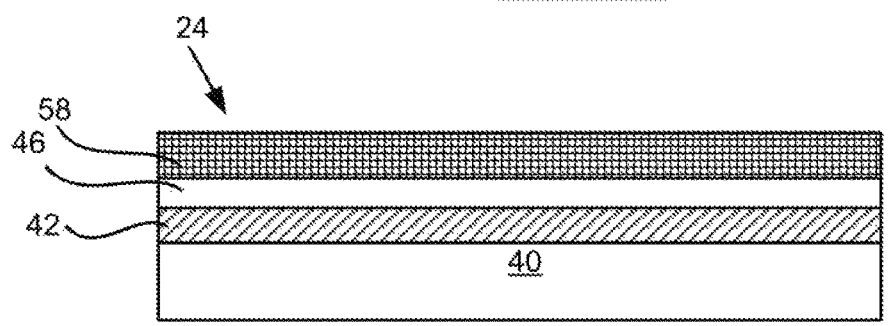
FIG. 8 is a cross-sectional view, not to scale, of a heating element having fluid absorbed into an upper porous surface according to an embodiment of the disclosure.

In the final step of the process, FIG. 7, the glass frit is sintered while on the heating element 24 to provide a porous surface 56 having a thickness ranging from about 0.5 millimeters to about 3 millimeters, such as from about 1 millimeter to about 2 millimeters. Upon ejecting fluid from the ejection head 22 onto the heating element 24, the fluid is absorbed by the sintered glass frit layer to form a fluid containing porous layer 58 (FIG. 8). The fluid containing layer 58 provides increased effective heating element surface area so that more efficient evaporation of the liquid may take place.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

What is claimed is:

1. A heating element for a vaporization device comprising a conductive material deposited onto an insulative substrate, a protective layer deposited onto the conductive layer, and a porous layer having a porosity of at least about 50% deposited onto the protective layer wherein the heating element has an effective surface area (ESA) for fluid vaporization that is greater than a planar surface area defined by dimensions of the heating element so that a fluid contact surface of the heating element is greater than the planar surface area of the heating element.

2. The heating element of claim 1, wherein the heating element has a rectangular shape and has an effective surface are for fluid vaporization defined by the equation ESA>L×W, wherein L is a length of the heating element and W is a width of the heating element.

3. The heating element of claim 1, wherein the porous layer has a grit blasted surface texture providing the effective surface area (ESA) thereof.

4. The heating element of claim 1, wherein the porous layer has a thickness ranging from about 0.5 millimeters (mm) to about 3 mm.

5. The heating element of claim 1, wherein the insulative substrate, conductive layer and protective layer have a combined thickness ranging from about 4 millimeters (mm) to about 1 centimeter (cm).

6. The heating element of claim 1, wherein the porous layer has a porosity ranging from about 50% to about 95%.

7. The heating element of claim 1, wherein the conductive layer is a screen printed conductive layer deposited onto a ceramic substrate.

8. The heating element of claim 1, wherein the porous layer comprises a laser etched ceramic layer.

9. The heating element of claim 1, wherein the porous layer comprises a coarse grit deposited ceramic layer that is sintered.

10. A vaporization device comprising a housing body, a mouthpiece attached to the housing body, and a heating element disposed adjacent to the mouthpiece for vaporizing fluid ejected from an ejection head, wherein the heating element comprises a conductive material deposited onto an insulative substrate, a protective layer deposited onto the conductive layer, and a porous layer having a porosity of at least about 50% deposited onto the protective layer.

11. The vaporization device of claim 10, wherein the heating element has a rectangular shape and has an effective surface area (ESA) for fluid vaporization defined by the equation ESA>L×W, wherein L is a length of the heating element and W is a width of the heating element.

12. The vaporization device of claim 11, wherein the porous layer has a grit blasted surface texture providing the effective surface area (ESA) thereof.

13. The vaporization device of claim 10, wherein the porous layer has a thickness ranging from about 0.5 millimeters (mm) to about 3 mm.

14. The vaporization device of claim 10, wherein the insulative substrate, conductive layer and protective layer have a combined thickness ranging from about 4 millimeters (mm) to about 1 centimeter (cm).

15. The vaporization device of claim 10, wherein the porous layer has a porosity ranging from about 50% to about 95%.

16. A method for vaporizing a fluid ejected by an ejection head so that substantially all of the fluid ejected by the ejection head is vaporized, comprising providing a vaporization device having an ejection head and a vaporizing heater element adjacent to the ejection head;
ejecting fluid onto the heater element;
activating the heating element during fluid ejection; and
vaporizing substantially all of the fluid using the heating element,
wherein the heating element comprises a conductive material deposited on an insulative substrate, a protective layer deposited on the conductive layer, and a porous layer having a porosity of at least about 50% deposited onto the protective layer.

17. The method of claim 16, further comprising absorbing the fluid by the porous layer of the heating element, wherein the porosity of the heating element is defined by the equation ESA>L×W, wherein ESA is an effective surface area of the heating element, L is a length of the heating element and W is a width of the heating element having a rectangular shape and that is exposed to a vaporizing fluid.

18. The method of claim 16, wherein the porous layer is deposited as a coarse glass frit that is sintered onto the protective layer of the heating element.

19. The method of claim 16, wherein the porous layer is formed by grit blasting the protective layer or a ceramic layer deposited onto the protective layer of the heating element.

20. The method of claim 16, wherein the porous layer is formed by laser etching the protective layer or a ceramic layer deposited onto the protective layer of the heating element.

\* \* \* \* \*